United States Patent [19]

Cassaday

[11] Patent Number: 4,678,641
[45] Date of Patent: Jul. 7, 1987

[54] ISOLATION LIQUID LAYER RETENTION DEVICE

[75] Inventor: Michael M. Cassaday, Valhalla, N.Y.

[73] Assignee: Technicon Instruments Corporation, Tarrytown, N.Y.

[21] Appl. No.: 879,918

[22] Filed: Jun. 30, 1986

[51] Int. Cl.$^4$ ............................................. B01L 11/00
[52] U.S. Cl. ..................................................... 422/101
[58] Field of Search ............... 73/864.91, 864.72, 864, 73/864.81, 864.22; 422/102, 63, 82, 100, 1, 99, 101

[56] References Cited

U.S. PATENT DOCUMENTS

| | | | |
|---|---|---|---|
| 3,479,141 | 11/1969 | Smythe et al. | 422/82 |
| 4,121,466 | 10/1978 | Reichler et al. | 73/864.22 |
| 4,391,779 | 7/1983 | Miskinis | 422/102 |
| 4,515,753 | 5/1985 | Smith et al. | 422/82 |

Primary Examiner—Stewart J. Levy
Assistant Examiner—Robert R. Raevis
Attorney, Agent, or Firm—Jeffrey M. Greenman; James J. Romano, Jr.

[57] ABSTRACT

A new and improved isolation liquid layer retention device is provided, and comprises a porous member operatively associated with the interior of a container which contains a quantity of an aqueous liquid having a layer of a generally immiscible isolation liquid which is generally of greater density disposed thereon. The porous member is operable to cause the aqueous liquid to form a generally convex meniscus to strongly support the generally denser isolation liquid layer thereon to prevent the sinking of the isolation liquid into the aqueous liquid; and is operable to act as a moderating control by virtue of a "source and sink" action vis-a-vis the isolation liquid to maintain a uniform and readily reproducible configuration for the isolation liquid layer on a container-to-container basis with regard to each of a plurality of the containers. The device is particularly adapted for use with a plurality of containers of aqueous sample and reagent liquids in contemporary automated sample liquid analysis systems.

14 Claims, 5 Drawing Figures

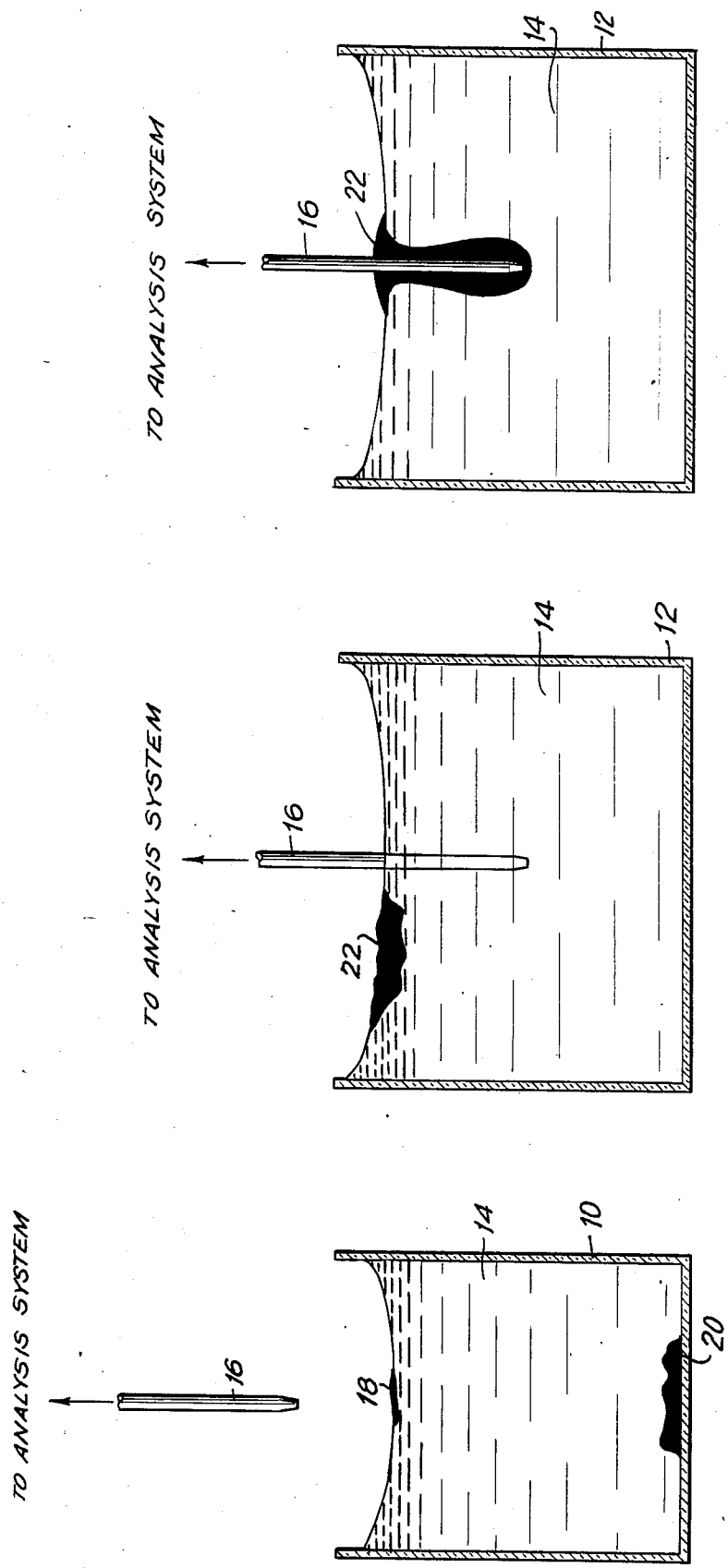

& #

ISOLATION LIQUID LAYER RETENTION DEVICE

BACKGROUND OF THE INVENTION

1. Field of the Invention

This invention relates to a new and improved isolation liquid layer retention device which is particularly adapted for use with aqueous sample and reagent liquid containers in automated sample liquid analysis systems which utilize the isolation liquid to minimize sample liquid carryover thereby optimizing the accuracy of the sample liquid analysis results. 2. Description of the Prior Art U.S. Pat. No. 4,515,753 issued May 7, 1985 to John L. Smith, et al for Integral Reagent Dispenser and assigned to the assignee hereof discloses, in FIGS. 8, 9 and 10, an isolation liquid lens yoke 290 comprising an isolation liquid lens loop 292 which floats upon the surface of an aqueous reagent liquid in a reagent liquid dispenser well, and which functions to centrally position a lens of an immiscible isolation liquid upon the surface of said reagent liquid for aspiration therefrom by an aspiration probe attendant reagent liquid aspiration. This lens loop comprises a hydrophobic fluoropolymer inner surface; but is not made of a porous material. As a result, this lens loop may not effectively function to prevent the isolation liquid, which may be of greater density than the aqueous reagent liquid, from sinking in whole or in part beneath the reagent liquid; nor does it effectively function to assure the presence of an isolation liquid layer of uniform and readily reproducible configuration atop the reagent liquid at all times attendant use of the dispenser with an automated sample liquid analysis system as described.

Each of U.S. Pat. Nos. 3,479,141, 4,121,466, 4,253,846 and 4,357,301 also discloses an automated sample liquid analysis system which makes use of an isolation liquid of the nature described hereinabove with regard to U.S. Pat. No. 4,515,753. None of these United States Patents discloses an isolation liquid retention device embodying the structure and function of the device of this invention.

SUMMARY OF THE INVENTION

As disclosed herein, the new and improved isolation liquid layer retention device of my invention comprises a porous, generally ring-shaped member which is disposed along the inner wall of a generally cylindrical container which contains a quantity of an aqueous liquid. A layer of an isolation liquid, which is generally of greater density than the aqueous liquid and generally immiscible therewith, is disposed atop the aqueous liquid quantity; and the porous ring-shaped member is in surface contact with both the aqueous liquid quantity and the isolation liquid layer. The porous member is made of a material of very low surface energy which is selectively wettable by the isolation liquid to the substantial exclusion of the aqueous liquid. As a result of the low surface energy material of the porous member, a generally convex meniscus is formed by the aqueous liquid to provide a high level of mechanical support for the isolation liquid layer and attendant resistance to the sinking thereof into the generally less dense aqueous liquid. In addition, this generally convex meniscus operates to cause the isolation liquid layer to reside principally at the interior walls of the container, as opposed to the central portion thereof as would be the case with a concave meniscus. As a result of the porosity of the member, the selective wettability thereof by the isolation liquid to the substantial exclusion of the aqueous liquid, and the "source and sink" action of the porous member vis-a-vis the isolation liquid, a particularly stable isolation liquid layer of uniform readily reproducible configuration when viewed on a container-to-container basis for each of a plurality of containers, is provided. The isolation liquid layer retention device is particularly adapted for use with aqueous sample and reagent containers in contemporary automated sample liquid analysis systems; and is readily and economically disposable after only one such use.

OBJECTS OF THE INVENTION

It is accordingly an object of my invention to provide a new and improved isolation liquid layer retention device for retaining an isolation liquid layer in position on the surface of a generally less dense and immiscible aqueous liquid quantity in a container.

It is another object of my invention to provide an isolation liquid layer retention device as above which is operable to retain said isolation liquid layer in uniform and readily reproducible configuration when viewed on a container-to-container basis for each of a plurality of containers.

It is another object of my invention to provide an isolation liquid layer retention device as above which is readily and conveniently utilizable with a wide variety of different aqueous liquid containers.

It is another object of my invention to provide an isolation liquid layer retention device as above which is of such simple and low cost construction as to be readily disposable in economically feasible manner after but a single use.

It is a further object of my invention to provide an isolation liquid layer retention device as above which is particularly adapted for use with aqueous sample and reagent liquid containers in contemporary automated sample liquid analysis systems.

DESCRIPTION OF THE DRAWINGS

The above and other objects and significant advantages of my invention are believed made clear by the following detailed description thereof taken in conjunction with the accompanying drawings wherein:

FIGS. 1, 2 and 2A are respectively vertical cross-sectional views of sample or reagent liquid containers to clearly illustrate the problems of the prior art;

DETAILED DESCRIPTION OF THE INVENTION

Figure 4:
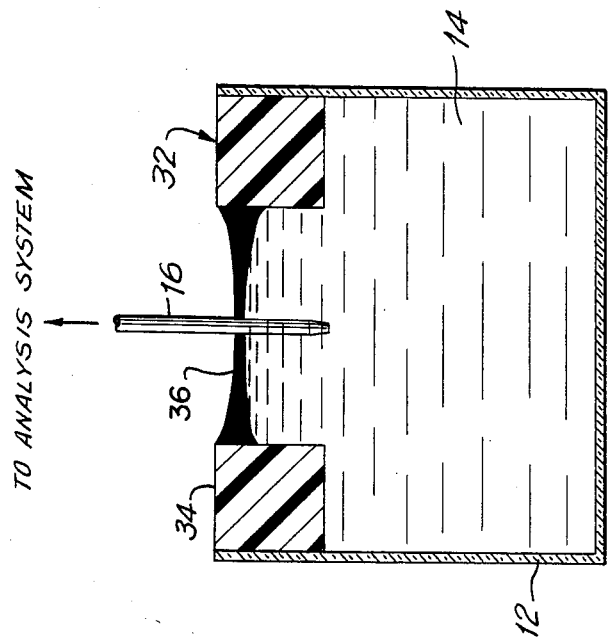
FIG. 4 is a vertical cross-sectional view of the container of FIG. 2 incorporating a second embodiment of an isolation liquid layer retention device configured and operable in accordance with the teachings of my invention.

FIGS. 1 and 2 illustrate the significant problems of the prior art as are effectively remedied by the apparatus of this invention; and, to that effect, depict containers 10 and 12 made of glass or like material for the containment of aqueous sample or reagent liquids 14 in the environment of an automated sample liquid analysis system of the nature of those disclosed in U.S. Pat. Nos. 3,479,141, 4,121,466, 4,253,846, 4,357,301 and 4,515,753, the disclosures of which are hereby incorporated by reference herein.

As briefly described for purposes of this disclosure, these automated sample liquid analysis systems, which operate to automatically analyze in turn each of a series of appropriately reacted sample liquids as supplied thereto in sequence from separate containers, utilize an isolation liquid, for example a fluorocarbon liquid, which is substantially immiscible with the aqueous sample and reagent liquids, and which selectively "wets" fluorinated hydrocarbon or like material analysis system components in the nature of aspirating and/or dispensing probes, system conduits and the like, to the substantial exclusion of the aqueous sample and reagent liquids; thereby effectively minimizing sample liquid carryover, e.g. the contamination of a succeeding sample liquid by the residue of a preceding sample liquid, with resultant significant increase in sample liquid analysis accuracy.

In analysis system operation, carefully predetermined, like quantities of this isolation liquid, which is generally of greater density than the respective sample or reagent liquids 14, are carefully layered in any convenient manner atop the meniscus of each of those liquids for retention thereon by surface tension in the form of an isolation liquid layer or "lens" which covers the surface of the sample or reagent liquid and which is of carefully predetermined thickness at the critical central area of that surface. Upon presentation of the thusly isolation liquid-layered containers 10 or 12 to the analysis system off-take position, an aspirating probe 16, which is made from an appropriate fluorinated hydrocarbon material in the nature of Teflon which is selectively "wettable" by the isolation liquid to the substantial exclusion of the sample or reagent liquids, and which is centrally disposed as shown relative to the containers 10 and 12, is automatically inserted into the containers in turn as illustrated by FIG. 2 for a carefully predetermined time and to a carefully predetermined extent. This, of course, results in the piercing of the isolation liquid layer by the aspirating probe and the extension of the latter into the sample or reagent liquid in the container of interest; and accomplishes the aspiration and supply as indicated to the analysis system of a carefully predetermined quantity of the isolation liquid followed by a carefully predetermined quantity of the sample or reagent liquid as the case may be. The thusly aspirated and supplied isolation liquid quantity is effective within the analysis system to greatly inhibit sample liquid carryover as described hereinabove; while the surface contact of the isolation liquid layer with the selectively "wettable" outer surface of the fluorcarbon aspirating probe 16 to the substantial exclusion of the sample liquids attendant the piercing of that layer by the probe as the same is inserted as described into the container of interest will, of course, greatly inhibit the sample liquid from adhering thereto and contaminating subsequently probe-aspirated samples.

Two major shortcomings, both of which can operate to significant disadvantage with regard to overall sample liquid analysis system accuracy, have been determined by applicant to exist with regard to the above and are respectively illustrated by FIG. 1 and FIG. 2.

More specifically, FIG. 1 makes clear that the isolation liquid layer, as there indicated at 18, being of greater density than the sample or reagent liquid 14, will tend to sink in whole, or in part as shown at 20, below the surface of the liquid 14. This tendency is, of course, markedly increased by the liquid surface disturbance which results from the insertion of the aspirating probe 16 into the container 10 as described, and by agitation of the liquid 14 which results from the indexing or like movement of the container 10 into the analysis system off-take position. If this occurs, the thickness of the isolation liquid layer, if any, remaining atop the liquid 14 will in the vast majority of instances be reduced to a not insignificant degree. This results in less than the carefully predetermined quantity of isolation liquid being aspirated by the aspiration probe 16 with attendant unacceptable variation in sample liquid carryover inhibition by the isolation liquid within the analysis system; and also results in more than the carefully predetermined quantity of the sample or reagent liquid 14 being aspirated by the aspirating probe 16 with attendant unacceptable variation in the precision of sample liquid analysis system operation. Of course, the above combine to result in unacceptable degradation in the accuracy of the sample liquid analysis results; and this is especially true in highly precise contemporary automated sample liquid analysis systems which operate with greatly reduced sample, reagent and isolation liquid quantities.

FIG. 2 which depicts a container 12 of somewhat greater diameter than the container 10 of FIG. 1, illustrates the problematic situation wherein although no part of the isolation liquid layer or "lens" as there indicated at 22 sinks below the surface of the sample or reagent liquid 14, the same nonetheless becomes laterally displaced from the central portion of the liquid surface in the container. As a result, it will be clear that the aspirating probe 16 will totally miss the isolation liquid layer 22 upon the insertion of the probe into the container 12 as shown in FIG. 2. Thus, no isolation liquid will be aspirated by the probe 16 for supply to the sample liquid analysis system for essential minimization of sample liquid carryover as described hereinabove, and, no protection of the outer surface of the aspirating probe 16 against sample liquid carryover as described hereinabove will be provided by the isolation liquid 22. Again, and in this instance even more pronounced, unacceptable degradation in the accuracy of the sample liquid analysis results will occur.

With further regard to FIGS. 1 and 2, it will be clear to those skilled in this art that, since in each instance the interfacial tension—which may be approximated by the difference between the surface tension of the aqueous sample or reagent liquids and the surface tension of the glass container materials—is relatively low, a contact angle as depicted in FIG. 1 and FIG. 2 between the aqueous liquid surface and the container wall which gives a negative or concave aqueous liquid meniscus results. Under these circumstances, the surface tension of the isolation liquid, which as described hereinabove is generally denser than the aqueous liquids, simply becomes insufficient in the face of the force of gravity to maintain an isolation liquid layer which fully occludes the open end of the container atop the aqueous liquid; and especially in the face of the additionally isolation liquid layer-disruptive forces generated by the requisite container movement attendant container indexing, and aspirating probe insertion into and withdrawal from the container, all as described hereinabove.

An additional problem of significance occurs in accordance with the principles of the prior art as illustrated in FIG. 2A when the isolation liquid 22 neither sinks in whole or in part into the aqueous liquid as illustrated in FIG. 1, nor shifts away from the central portion thereof as illustrated in FIG. 2, but rather accumulates or "pools" at that central portion to form an isolation liquid layer or "glob" 23 of inordinate thickness at that central portion. Under these circumstances, it will be clear that insertion of the aspirating probe 16 into the central container portion as illustrated in FIG. 2A with resultant piercing by the probe of this isolation liquid "glob" will result in the aspiration by the probe of far too much isolation liquid and far too little, if any, aqueous sample or reagent liquid, to again give rise to totally unacceptable degradation in the accuracy of the sample liquid analysis results. Of course, in this instance the selective wettability of the probe by the isolation liquid to the substantial exclusion of the aqueous liquid makes the problem even worse by the drawing of the isolation liquid "glob" 23 to the probe 16 as shown in FIG. 2A.

Figure 3:
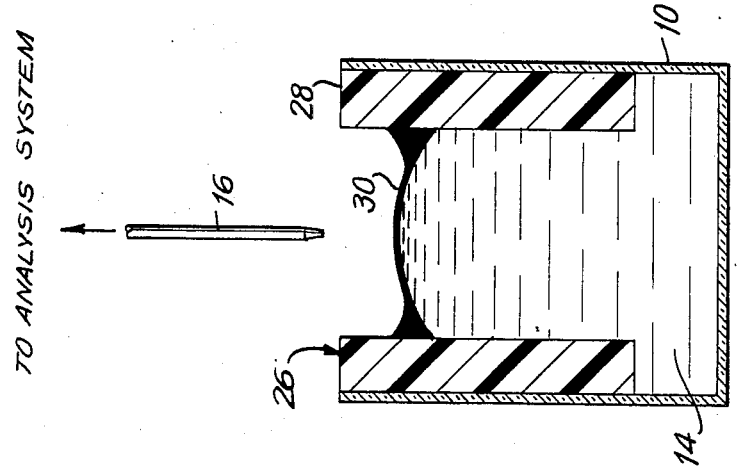
FIG. 3 is vertical cross-sectional view of the container of FIG. 1 incorporating a first embodiment of an isolation liquid layer retention device configured and operable in accordance with the teachings of my invention.

Referring now to FIG. 3, a first embodiment of an isolation liquid layer retention device representatively configured and operable in accordance with the teachings of my invention is indicated generally at 26 and comprises a porous ring 28 of an appropriately inert material of very low surface energy characteristics which is disposed and positioned as shown in any suitable manner within the container 10 in surface contact with the inner container wall to surround the opening in the container 10 into which the aspirating probe 16 is inserted as described hereinabove for aspiration of the aqueous liquid 14. A preferred material for the ring 28 is a fluorinated hydrocarbon in the nature of Teflon which is of very low surface energy; and which provides the additional advantage of being selectively "wettable" by the isolation liquid to the substantial exclusion of the aqueous sample and reagent liquids. For purposes of this invention as set forth in detail hereinbelow, the material of the ring 28 is made porous.

With the porous ring 28 constituted and positioned as described in the substantially aqueous liquid filled container 10, it will be clear that the high interfacial tension between the aqueous sample or reagent liquid 14 and the ring 28 resulting from the very low surface energy of the ring material will in turn result in a contact angle between the aqueous liquid and the ring which forms a positive or convex aqueous liquid meniscus as shown in FIG. 3. Accordingly, and upon the disposition of the isolation liquid as indicated at 30 in FIG. 3 atop the convex aqueous liquid meniscus, it will be clear that significantly increased mechanical support —when compared to that provided by the concave aqueous liquid meniscuses of the prior art as illustrated and described hereinabove with regard to FIG. 1 and FIG. 2—will be provided for the layer of the isolation liquid 30. Thus, sinking in whole or in part of the isolation liquid layer 30 beneath the surface of the aqueous sample or reagent liquid 14 of FIG. 3 will be greatly, and of course most advantageously insofar as the overall accuracy of the sample liquid analysis results is concerned, inhibited by the teachings of my invention.

In addition to the above, it will be clear that the natural reservoir, or what may be termed the "source and sink," action of the porous ring 28 vis-a-vis the isolation liquid 30, coupled with the surface tension-driven selective "wetting" of the porous ring 28 by the isolation liquid 30 to the substantial exclusion of the aqueous liquid 14, will function to displace the aqueous liquid 14 away from the relevant interior wall surface of the porous ring 28 in such manner that the isolation liquid 30 is drawn to that ring wall surface. This greatly inhibits "pooling" of the isolation liquid 30 atop the aqueous liquid 14 at an off-center location thereon as described hereinabove with regard to FIG. 2, or at the critical central portion thereof as described hereinabove, both to significant disadvantage; and instead greatly promotes the particularly advantageous occlusion of the entire open container end, and the covering of the entire exposed aqueous liquid surface, by the isolation liquid 30 as shown in FIG. 3. Of course, the fact that the isolation liquid 30 does not "pool" as described even further reduces the probability of the same accumulating in a single mass atop the aqueous liquid 14 and reaching a weight which will cause it to penetrate the aqueous liquid meniscus and sink in the container 10; it being clear to those skilled in this art that this would be of particular concern if the isolation liquid "pools" and sinks around the aspirating probe 16 at the critical central portion of the aqueous liquid 14 attendant probe insertion for aqueous liquid aspiration and resultant disturbance by the probe of the isolation liquid-supporting surface tension of the aqueous liquid 14, in which event primarily isolation liquid as opposed to aqueous liquid as required would be apsirated by the probe 16.

With regard to the uniformity of isolation liquid distribution, and attendant uniformity of isolation liquid layer thicknesses, atop the aqueous sample or reagent liquids 14 in each of a series of ringed containers 10 of FIG. 3 as would be required for operation of contemporary automated sample liquid analysis systems, it will be clear that the same are greatly promoted to significant advantage by the moderating control on isolation liquid layer configuration provided by the "source and sink" effects of the teachings of my invention in that too rich a disposition of the isolation liquid 30 atop the aqueous sample or reagent liquids 14 in one or more of a series of the ringed containers 10 of FIG. 3 will simply result, within reasonable limits of course, in more isolation liquid 30 being absorbed by the porous ring 28; while too lean an isolation liquid disposition as above in one or more of the same series of ringed containers 10 will simply result, again within reasonable limits, in less isolation liquid 30 being absorbed by the porous ring 28. Thus, generally compound concave lens-shaped isolation liquid layers 30 of unifrom overall thickness and volume and, more critically of unifrom and readily reproducible thickness and volume at the respective critical central portion thereof which are pierced in turn by the aspirating probe 16 upon the successive presentation of the ringed containers 10 thereto for sample or reagent liquid aspiration and supply in turn to the sample liquid analysis system as described, will be provided on each of the series of ringed containers 10 of FIG. 3 under discussion; whereby the aspiration and supply in turn by the probe 16 to the sample liquid analysis system of the same carefully predetermined and readily reproducible volumes of the isolation liquid 30, and of the aqueous sample or reagent liquids 14 as the case may be be, from each of the series of containers under discussion is assured. Of course, this would also hold true for repeated aspirations by the aspirating probe 16 of aqueous sample or reagent liquids from the same ringed container 10. In each instance, these like isolation liquid volumes are carefully predetermined in accordance with the internal operational requirements of the sample liquid analysis system with regard to the optimal minimization of sample liquid carryover. In addition, the requirement for sufficient protection by the isolation liquid layer 30 in each instance of the relevant external surface portion of the aspirating probe 16 to minimize sample liquid carryover as described from that source will also play a role in determining the overall configuration of the isolation liquid layer.

The depth of the porous ring 28 vis-a-vis the depth of the container 10 is carefully predetermined to be more than sufficient to accomodate the entire dynamic fill range of the container in accordance with the relevant operational characteristics of the automated sample liquid analysis system; it being clear to those skilled in this art that this dynamic fill range can be quite extensive relative to the overall depth of the container in those instances wherein repeated aqueous sample or reagent liquid quantities are to be asprirated in turn by the aspirating probe 16 from the same ringed container 10 of FIG. 3.

Referring now to FIG. 4 which again depicts the container 12 as being of somewhat greater diameter than the container 10 of FIG. 3, a second embodiment of an isolation liquid layer retention device representatively configured and operable in accordance with the teachings of my invention is indicated generally at 32 and again comprises a porous ring 34 which is complementally configured relative to the container 12 so as to fit therewithin at the upper portion of the container, thereby effectively reducing the internal diameter of the larger open container end to a significant degree. Since the container 12 is of substantially greater volume than the container 10, it will be clear that the dynamic fill range thereof attendant utilization in an automated sample liquid analysis system will probably be smaller that that of the container 10; and FIG. 4 accordingly illustrates the versatility of the porous ring of my invention by making clear that the same may be of significantly lesser depth vis-a-vis the overall depth of the container for use in such instances. In addition, FIG. 4 makes clear that the porous ring 34 is of substantially greater thickness than the porous ring 28 of FIG. 3, thus effectively and advantageously reducing the larger diameter of the open end of the larger container 12 to a significant degree; it being clear to those skilled in this art that this results in the like significant reduction in the diameter of the meniscus of the aqueous liquid 14 thereby rendering the same more effective with regard to the essential support of the isolation liquid layer as there indicated at 36, and promoting the essential full occlusion by the isolation liquid layer of the open end of the ringed container 12.

In all other material respects, the porous ring 34 of FIG. 4 is identical to the porous ring 28 of FIG. 3, and accordingly functions in the manner described in detail hereinabove with regard to the latter to effectively and advantageously retain an appropriately configured isolation liquid layer 36 atop the aqueous sample or reagent liquid 14 in the ringed container 12 as shown.

Parameters which may be readily and conveniently varied within reasonable limits consistent with the essential operational characteristics of the automated sample liquid analysis system to determine the overall configuration of the isolation liquid layer in accordance with the teachings of my invention include; the composition of the isolation liquid; the composition of the porous ring; the density of the isolation liquid vis-a-vis the densities of the respective aqueous sample and reagent liquids then in use; the thickness and/or internal diameter of the porous ring vis-a-vis the internal diameter and depth of the containers required for sample liquid analysis; and the size of the pores in the porous ring, respectively; and it will be clear to those skilled in this art that proper selection of the above will provide for effective isolation liquid layer formation, and equilibrium operation and retention as described with significant dynamic stability for the layer throughout a wide range of operational conditions.

It is to be made clear that the term "uniform configuration" as utilized hereinabove with regard to the isolation liquid layer relates to the configuration thereof on a container-to-container basis within the context of a multi-container automated sample liquid analysis system, and relates to the configuration thereof in the context of repeated aqueous sample or reagent liquid aspirations from the same container; and is, in either event, of particular importance with regard to the generally central portion of the isolation liquid layer which is pierced as described by the aspirating probe 16 attendant aqueous liquid aspiration from the container.

The new and improved isolation liquid layer retention device of my invention is particularly adapted for use in the reagent dispensing wells of automatically refillable reagent dispensers of the nature disclosed in U.S. Pat. No. 4,515,753 wherein excess accumulation of the isolation liquid at the bottom of the dispensing well due to sinking of the same in the aqueous reagent liquid can, attendant prolonged dispenser operation and-often repeated reagent liquid aspirations therefrom, reach such a high level that isolation liquid rather than reagent liquid is ultimately aspirated by the analysis system aspirating probe upon the penetration thereby of the isolation liquid level in question. In addition, this large accumulation of the isolation liquid at the bottom of the dispensing well can ultimately reach such proportion as to significantly interfere with the dispenser fill mechanism which operates to automatically replenish the reagent liquid supply in the reagent dispensing well via a supply passage operatively connected to the bottom of the dispensing well. Of course, both of these eventualities result in totally unacceptable degradation in the accuracy of the sample liquid analysis results; and are prevented, within reasonable limits as discussed, by the new and improved isolation liquid layer retention device of my invention.

By all of the above is believed made clear that the isolation liquid layer retention device of my invention will, in full accordance with the stated objects thereof, provide for the simple, economical and particularly effective minimization of sample liquid carryover in automated sample liquid analysis systems with attendant optimization of the accuracy of the sample liquid analysis results.

Although representatively disclosed as operable in conjunction with containers made of glass, it will be clear that the isolation liquid layer retention device of my invention would also be operable with no loss in functional effectiveness in conjunction with containers made of other and different materials, for example an appropriately inert plastic in the nature of polyethylene which, as a result of the surfactant which is always present in the sample and reagent liquids attendant the automated analysis of the former as described, would normally form a concave meniscus with those liquids. Too, it is believed clear that the device of my invention need not, of operational necessity, be ring-shaped; but that the same could alternatively, for example, be of generally rectangular configuration for use with containers or compartments of that general configuration in horizontal cross-section as disclosed in U.S. Pat. No. 4,357,301.

The isolation liquid layer retention device of my invention may be fixedly secured in the container in any convenient manner, for example by a relatively low force fit, or by a suitable epoxy. Alternatively, and for use in instances wherein the material of the ring is of lesser density than the aqueous sample and reagent liquids, the device may be free-floating on, or to an appropriate extent in, the aqueous liquids with only the slightest of clearances, not shown, between the ring and the interior wall of the container provided to enable the ring to automatically adjust as required to the level of the aqueous liquid in the container.

Of course, the extreme simplicity and low cost of the isolation liquid layer retention device of my invention render disposal thereof after but a single use economically feasible; and, of course, most desirable from the standpoint of sample liquid carryover minimization.

Although representatively disclosed herein as applied to use in conjunction with containers containing aqueous liquids, it will be understood by those skilled in this art that the teachings of my invention are not limited thereto, but rather, are also applicable to use in conjunction with containers containing non-aqueous liquids in the nature, for example, of non-aqueous industrial liquids. Again, the isolation liquid will, of course, be immiscible with these non-aqueous liquids; and will selectively wet the isolation liquid layer retention device of my invention to the substantial exclusion thereof.

Various changes may be made in the hereindisclosed preferred embodiments of my invention without departing from the spirit and scope of that invention as defined in the appended claims.

What is claimed is:

1. In an open container which contains a quantity of a first liquid and a layer of a denser isolation liquid which is generally immiscible with said first liquid and which is disposed atop said first liquid in surface contact therewith, the improvements comprising, an isolation liquid layer retention device operatively associated with said container, said device comprising a porous member which surrounds the surface of said liquid quantity and which contacts said first liquid and said isolation liquid layer to retain said isolation liquid layer in position atop said liquid quantity.

2. In a container as in claim 1 wherein, said porous member is made of a material having a low surface energy to provide a convex meniscus for said liquid quantity in said container for support of said isolation liquid layer thereon.

3. In a container as in claim 1 wherein, said porous member is made of a material which is selectively wettable by said isolation liquid to the substantial exclusion of said first liquid.

4. In a container as in claim 1 wherein, said porous member is disposed at least in part at the top of said open container.

5. In a container as in claim 1 wherein, said porous member is disposed within the upper portion of said container, and extends therewithin both above and below the level of said liquid quantity.

6. In a container as in claim 5 wherein, the level of said liquid quantity in said container is variable throughout a predetermined range, and wherein the vertical extent of said porous member in said container is at least equal to said range.

7. In a container as in claim 1 wherein, said container is generally cylindrical, and said porous member is generally ring shaped.

8. In a container as in claim 7 wherein, the outer wall of said generally ring shaped porous member is in surface contact with the internal wall of said generally cylindrical container, and the internal diameter of said porous member is less than the internal diameter of said container.

9. In a container as in claim 1 wherein, said porous member is fixedly secured in said container.

10. In a container as in claim 1 wherein, said porous member is free-floating on said first liquid in said container, with clearance between said porous member and said container.

11. In a container as in claim 1 wherein, said porous member comprises an opening which is smaller than the opening in said container, and wherein said porous member is operable to block access to said first liquid in said container except through said opening in said porous member.

12. In a container as in claim 1 wherein, said first liquid is an aqueous liquid.

13. In a container as in claim 1 wherein, said first liquid is a non-aqueous liquid.

14. In a container as in claim 1 wherein, said porous member is in surface contact with the internal wall of said container.

* * * * *